United States Patent [19]

Drent

[11] Patent Number: 5,149,868
[45] Date of Patent: Sep. 22, 1992

[54] CARBONYLATION PROCESS

[75] Inventor: Eit Drent, Amsterdam, Netherlands

[73] Assignee: Shell Oil Company, Houston, Tex.

[21] Appl. No.: 671,316

[22] Filed: Mar. 19, 1991

[30] Foreign Application Priority Data

Dec. 3, 1990 [GB] United Kingdom ............... 9026211

[51] Int. Cl.$^5$ .................................... C07C 51/10
[52] U.S. Cl. .................... 562/497; 562/406;
562/522; 560/114; 560/207
[58] Field of Search ............... 560/114, 207; 562/497, 562/406, 522

[56] References Cited

U.S. PATENT DOCUMENTS

| 4,670,582 | 6/1987 | Drent | 560/114 |
| 4,739,109 | 4/1988 | Drent | 560/114 |
| 4,739,110 | 4/1988 | Drent | 560/114 |

FOREIGN PATENT DOCUMENTS

| 055875 | 11/1981 | European Pat. Off. |
| 106379 | 8/1983 | European Pat. Off. |
| 168876 | 7/1985 | European Pat. Off. |
| 280380 | 2/1988 | European Pat. Off. |

Primary Examiner—Paul J. Killos

[57] ABSTRACT

A process for the carbonylation of olefinically or alkynically unsaturated compounds with carbon monoxide in the presence of water and a catalyst, wherein the catalyst is based on a) a palladium compound,
b) a phosphine general formula $PR^1R^2R^3$, wherein $R^1$, $R^2$ and $R^3$ are the same or different each represent an alkyl, cycloalkyl or aryl group, at least one of which carries a substituent selected from the group consisting of a sulphonic acid, phosphonic acid and carboxylic acid groups, or a salt thereof, and
c) an anion of an acid having a $pK_a<3$ (measured in water at 18° C.) except hydrohalogenic acids, and wherein the reaction medium is at least initally a multiphase liquid reaction medium.

17 Claims, No Drawings

CARBONYLATION PROCESS

FIELD OF THE INVENTION

The invention relates to a process for the carbonylation of olefinically or alkynically unsaturated compounds with carbon monoxide.

BACKGROUND OF THE INVENTION

Processes for the carbonylation of olefinically or alkynically unsaturated compounds in the presence of a hydroxy compound, an acid or water are well-known, and have been described e.g. in European Patent No. 0,055,875, European Patent No. 0,106,379, European Patent No. 0,168,876 and European Patent No. 0,186,228, in which process a palladium catalyst system is employed. Generally such a process is conducted by introducing the various reactants and the catalyst into the reactor and allowing the carbonylation reaction to proceed under the desired conditions. Frequently the reaction medium includes a solvent to promote the solubility or miscibility of the reactants and/or to reduce the viscosity of the reaction medium.

With one of these types of carbonylation processes, i.e. the carbonylation of olefinically unsaturated compounds in the presence of water, it was observed that sometimes the rate of reaction, as measured by the degree of conversion of the olefin reactant within a given time, was reduced to an unacceptably low level.

An investigation carried out by the Applicant into the cause of the reduction in the rate of reaction, indicated that said phenomenon could well be related to formation of a reaction medium having more than one liquid phase, hereinafter referred to as multi-phase liquid reaction medium, as a result of insufficient miscibility of the liquid olefin or alkyne reactant and water, even when said reaction medium included a solvent.

The problem underlying the present invention is developing a process for the carbonylation of olefins or alkynes with carbon monoxide and in the presence of water, which does not suffer from the disadvantage as mentioned hereinbefore.

As a result of extensive research and experimentation it was found that the carbonylation of olefins or alkynes with carbon monoxide in the presence of water and a multi-phase liquid reaction medium, can advantageously be conducted in the presence of palladium catalyst compositions which include selected substituted phosphine ligands.

SUMMARY OF THE INVENTION

The invention therefore provides a process for the carbonylation of olefinically or alkynically unsaturated compounds with carbon monoxide in the presence of water and a catalyst, wherein the catalyst is based on
a) a palladium compound,
b) a phosphine of general formula $PR^1R^2R^3$, wherein $R^1$, $R^2$ and $R^3$ each represent an alkyl, cycloalkyl or aryl group, at least one of which carries a substituent selected from the group consisting of sulfonic acid, phosphonic acid and carboxylic acid groups, or a salt thereof, and
c) an anion of an acid having a $pK_a < 3$ (measured in water at 18° C.), except hydrohalogenic acids,
and wherein the reaction medium is at least initially a multi-phase liquid reaction medium.

DESCRIPTION OF THE PREFERRED EMBODIMENTS

The palladium compounds are preferably cationic compounds such as for example the salts of palladium with, for instance, nitric acid, sulfuric acid or alkanecarboxylic acids having not more than 12 carbon atoms. Salts of hydrohalogenic acids may, in principle, be used as well, but they have the drawback that the halogen ion may have a corrosive effect. Moreover, palladium complexes may also be used, for instance palladium acetylacetonate, tetrakis(triphenylphosphine)palladium, bis(tri-o-tolylphosphine)palladium acetate or bis(triphenylphosphine)palladium sulfate. Palladium acetate is a preferred palladium compound for the catalyst composition of the present invention to be based upon.

The groups $R^1$, $R^2$ and $R^3$ of the phosphine of general formula $PR^1R^2R^3$ (component b) may be the same or different; suitable phosphines thus include triarylphosphines, trialkylphosphines as well as alkyl diaryl phosphines and aryl dialkyl phosphines, wherein at least one of the groups R carries a substituent as specified hereinbefore. A further group of suitable phosphines of formula $PR^1R^2R^3$ are phosphines wherein $R^3$, being a group not carrying a substituent as specified hereinbefore, represents a chain of carbon atoms ending with a group $PR^4R^5$, in which $R^4$ and $R^5$ each represent an alkyl, cycloalkyl or aryl group. It is understood that these groups may be substituted with one or more substituents which do not interfere with the reaction. Preferably $R^4$ and $R^5$ are equal to $R^1$ and $R^2$, respectively. The chain of carbon atoms suitably comprises 2 to 6 carbon atoms, and preferably 2 to 3. The groups $R^1$, $R^2$, $R^3$, $R^4$ and $R^5$ which do not carry a substituent as specified hereinbefore, may be substituted with for example one or more halogen atoms, alkyl, aryl, alkoxy, acyl or trihalogenmethyl groups; alkoxy groups, especially methoxy groups, and halogen groups, especially chloro groups, being preferred such substituents.

Preferably, the aryl groups which may be present in the phosphines as mentioned hereinbefore are phenyl groups. Preferred phosphines $PR^1R^2R^3$ as component (b) of the catalyst composition are based on triphenylphosphines and alkyldiphenylphosphines. The substituents are preferably sulfonic acid groups or the alkali metal or ammonium salts thereof, sodium sulfonate type substituents being especially preferred.

As mentioned hereinbefore one or more of the groups R of the phosphines of general formula $PR^1R^2R^3$ carry a substituent as specified hereinbefore. Examples of preferred triarylphosphines wherein one or more of groups R carry a specified substituent include sodium 4-(diphenylphosphino)benzenesulfonate, phenyl-bis-(sodium 4-sulfonatophenyl)phosphine. Examples of preferred alkyl(diaryl)phosphines include sodium 2-(diphenylphosphino)ethanesulfonate and sodium 3-(diphenylphosphino)propanesulfonate. The present substituted phosphines can be obtained by processes as described in European Patent No. A-280380.

Effective catalyst systems generally comprise at least one mole of phosphine per gram atom of palladium. With the process of the present invention, it is preferred that the phosphine is employed in an amount which corresponds with at least 5 mol of phosphine per gram atom of palladium and more preferably with 10–150 mol of phosphine per gram atom of palladium, when the phosphine comprises one phosphorus atom.

Acids providing anions in the catalyst compositions for use in the process of the invention preferably have a non-coordinating anion, by which is meant that little or no co-valent interaction takes place between the palladium and the anion. Typical examples of such anions are $PF_6^-$, $SbF_6^-$, $BF_4^-$ and $ClO_4^{c-}$.

Acids preferably used are, for instance, sulfonic acids and those acids that can be formed, possibly in situ, by interaction of a Lewis acid such as, for example, $BF_3$, $AsF_5$, $SbF_5$, $PF_5$, $TaF_5$ or $NbF_5$ with a Bronsted acid such as, for example, a hydrohalogenic acid, in particular HF, phosphoric acid or sulfuric acid. Specific examples of the last-named type of acids are fluorosilicic acid, $HBF_4$, $HPF_6$ and $HSbF_6$. Typical sulfonic acids that can be used are fluorosulfonic acid, chlorosulphonic acid, p-toluenesulfonic acid and trifluoromethanesulfonic acid; the last two acids being preferred.

Catalyst compositions comprising a phosphine of general formula $PR^1R^2R^3$, wherein at least one of the groups $R^1$, $R^2$ or $R^3$ carries a substituent which is selected from the group of salts of sulfonic acid, phosphonic acid and carboxylic acid, as described hereinbefore, are novel.

The acids are preferably employed in an amount which corresponds with >2 equivalents $H^+$ per gram atom of palladium. When the $pK_a$ of the acid (component c) is considerably lower than the $pK_a$ of the acid on which the specified substituent is based, and of which at least one should be present in the phosphine $PR^1R^2R^3$, the number of equivalent $H^+$ of the acid (component c) per equivalent of said acid-derived substituent should be >1.

In a preferred embodiment of the present invention the catalyst compositions are not only based on components a), b) and c) but also include a source of anions, which anions have a hydrocarbyl moiety containing at least about 10 carbon atoms and are the conjugated base of an acid having a $pK_a < 3$ (measured in water at 18° C.).

In one embodiment said source of anions can be a component c) acid having a hydrocarbyl moiety containing at least about 10 carbon atoms. Preferred such acids are sulfonic acids and include alkylsulfonic acids, alkylarylsulfonic acids and hydroxyalkylsulfonic acids having at least 10 carbon atoms. Preferred such sulfonic acids have at least 15 carbon atoms per molecule.

In another embodiment the source of anion can be a salt, preferably an alkali metal or ammonium salt of an acid having a hydrocarbyl moiety containing at least about 10 carbon atoms and a $pK_a < 3$ (measured in water at 18° C.), as described hereinbefore. Sodium 4(octadecyl)-p-xylenesulfonate is a preferred sulfonate type anion source in view of its availability.

Catalyst compositions, which are not only based on components a), b) and c) but also include a source of anions as specified hereinbefore, are novel.

The amount of catalyst to be employed in said process is not critical and may vary over wide ranges. Preferably, the amount of catalyst used corresponds with about $10^{-5}$ to about $10^{-1}$ gram atom of palladium per mol of olefinically or alkynically unsaturated compound.

The olefinically or alkynically unsaturated compound may be an unsubstituted or substituted linear, branched or cyclic compound preferably having 2 to about 30, and in particular 2 to about 20, carbon atoms and preferably 1 to about 3 double, respectively triple bonds. The unsaturated compounds may be substituted, for instance, with one or more halogen atoms or cyano, ester, alkoxy, hydroxy, carboxy or aryl groups. If the substituents are not inert under the reaction conditions, the carbonylation reaction may be accompanied with other reactions. Examples of suitable olefinic compounds are ethene, propene, butene-1, butene-2, isobutene, cyclopentenes, the isomeric pentenes, hexenes, octenes and dodecenes, 1,5-cyclooctadiene, cyclododecene, 1,5,9-cyclododecatriene, allyl alcohol, methyl acrylate, ethyl acrylate, methyl methacrylate, acrylonitrile, acrylamide, N,N-dimethyl acrylamide, vinyl chloride, allyl chloride, acrolein, oleic acid, methyl allyl ether and styrene. Examples of suitable alkynes include propyne, 1-butyne, 2-butyne, 1-pentyne, 1-hexyne, 1-heptyne, 1-octyne, 2-octyne, 4-octyne, 5methyl-3-heptyne, 4-propyl-2-pentyne, 1-nonyne, phenylethyne and cyclohexylethyne.

The molar ratio wherein water and the olefinically or alkynically unsaturated compounds may be employed in the process, is not critical and may vary over wide ranges. Preferably the number moles of water per equivalent of olefinic or alkynic unsaturation is >1.

In the process according to the invention the carbon monoxide may be used pure or diluted with an inert gas, such as nitrogen, noble gases or carbon dioxide. Generally the presence of more than about 10% v (percent by volume) of hydrogen is undersirable, since under the reaction conditions it may cause hydrogenation of the olefinic or alkynic compound. Generally preference is given to the use of carbon monoxide or a carbon monoxide-containing gas which contains less than about 5% v of hydrogen.

The carbonylation according to the invention is preferably carried out at a temperature in the range between about 50° C. and about 200° C., in particular between about 75° C. and about 150° C. The overall pressure preferably lies between 1 and about 100, in particular between about 20 and about 75, bar gauge.

It was stated hereinbefore that the liquid reaction medium should at least initially be a multi-phase liquid reaction medium, as it is conceivable that the multi-phase reaction medium will be converted to a single-phase liquid reaction medium as the reaction progresses.

The process according to the present invention may be carried out batchwise, continuously or semi-continuously.

The products which may be prepared via the process as described hereinbefore will, depending on the functionality of the olefin or alkyne reactant, generally be mono-or polycarboxylic acids having a number of carbon atoms which equals that of the olefin or alkyne reactant plus one for every olefinically or alkynically unsaturated group reacted per molecule of said reactant. When the reaction products are derived from alkynically unsaturated reactants, they will have an $\alpha$-$\beta$-olefinically unsaturated moiety in the molecule. When the molar excess of water employed is not very large, it is possible that some of the formed carboxylic acid will be further reacted to anhydride.

The compounds prepared according to the process of the present invention may conveniently be isolated from the reaction mixture by known techniques, such extraction or distillation.

The products which may be prepared by the present process may be used as precursors for the preparation of e.g. fine chemicals.

The invention will be further illustrated with the following examples which are intended to be illustrative and which are not to be construed as limiting the invention.

EXAMPLE I

Into a 250 ml stainless steel (Hastelloy C) autoclave were introduced 40 ml diethylene glycol dimethyl ether, 10 ml water, 0.1 mmol palladium acetate, 2 mmol paratoluenesulfonic acid, 4 mmol of phenyl-bis(sodium 4-sulfonatophenyl)phosphine and 20 ml cyclopentene. Subsequently the reactor was closed and the air removed by pressuring/depressuring cycles with carbon monoxide, which was followed by carbon monoxide addition at a pressure of 40 bar and heating to 110° C. After a reaction time of 5 hours the reactor contents were cooled to room temperature (approx. 20° C.) and analyzed via gas liquid chromatography which showed an olefin conversion of 75% to cyclopentane carboxylic and with a selectivity of 100%.

EXAMPLE II

The procedure of Example I was repeated except that 4 mmol of sodium 4-octadecyl-p-xylenesulfonate was also introduced into the reactor which resulted in an olefin conversion after 5 hours reaction of 85%.

COMPARATIVE EXPERIMENT A

The procedure of Example I was repeated with the exception that the sulphonate-containing phosphine was replaced with 5 mmol of triphenyl-phosphine. After 5 hours the olefin conversion was <5%.

COMPARATIVE EXPERIMENT B

The procedure of Experiment A was repeated with the exception that 4 mmol of sodium 4-octadecyl-p-xylenesulphonate was also introduced into the reactor. After 5 hours reaction the olefin conversion was found to be 30%.

What is claimed is:

1. A process for the carbonylation of olefinically or alkynically unsaturated compounds which comprises reacting said compounds with carbon monoxide in the presence of water and a catalyst comprising:
   a) a palladium compound,
   b) a phosphine of general formula $PR^1R^2R^3$, wherein $R^1$, $R^2$ and $R^3$ are the same or different and each represent an alkyl, cycloalkyl or aryl group, at least one of which carries a substituent selected from the group consisting of sulfonic acid, phosphonic acid and carboxylic acid groups, or a salt thereof, and
   c) an anion of an acid having a $pK_a<3$ (measured in water at 18° C.) except hydrohalogenic acids, and wherein the reaction medium is at least initially a multi-phase liquid reaction medium.

2. The process as claimed in claim 1, wherein the phosphine is selected from a triarylphosphine or an alkyl(diaryl)phosphine.

3. The process as claimed in claim 1, wherein the aryl groups are phenyl groups.

4. The process as claimed in claim 1, wherein said substituent is selected from the group consisting of sulfonic acid groups and the alkali metal or ammonium salt thereof.

5. The process as claimed in claim 4, wherein the substituent is a sodium sulfonate group.

6. The process as claimed in claim 5, wherein the phosphine containing a sodium sulfonate substituent is selected from the group consisting of sodium 4-(diphenylphosphino)benzenesulfonate, phenyl-bis(sodium 4-sulphonatophenyl)phosphine, tris-(sodium 4-sulphonatophenyl)phosphine, sodium 2-diphenylphosphino)ethanesulfonate and sodium 3-(diphenylphosphino)propane sulfonate.

7. The process as claimed in claim 1, wherein the palladium compound is a cationic palladium compound.

8. The process as claimed in claim 7, wherein the cationic palladium compound is palladium acetate.

9. The process as claimed in claim 1, wherein said acid is selected from the group consisting of p-toluenesulfonic acid and trifluoromethane sulfonic acid.

10. The process as claimed in claim 1, wherein the phosphine is present in an amount which corresponds with at least about 5 mol of phosphine per gram atom of palladium 11. The process as claimed in claim 1, wherein said acids in c) is present in an amount corresponding with >2 equivalents $H^+$ per gram atom of palladium.

12. The process as claimed in claim 1, wherein said catalyst additionally comprises a source of anions, wherein said anions have a hydrocarbyl moiety containing at least 10 carbon atoms and are the conjugated base of an acid having a $pK_a<3$ (measured in water at 18° C.).

13. The process as claimed in claim 12, wherein said anion source is selected from a sulfonic acid and a salt thereof.

14. The process as claimed in claim 13, wherein said source of anions is sodium 4-octadecyl-p-xylenesulfonate.

15. The process as claimed in claim 1, wherein said catalyst is employed in an amount corresponding with about $10^{-5}$ to about $10^{-1}$ gram atom of palladium per mol of olefinically or alkynically unsaturated compound.

16. The process as claimed in claim 1, wherein the number of moles of water per equivalent of olefinic or alkynic unsaturation is >1.

17. The process as claimed in claim 1, wherein said process is carried out at a temperature in the range of from about 50° C. to about 200° C. and a pressure in the range of from about 1 bar to about 100 bar.

* * * * *